United States Patent
Calle et al.

(10) Patent No.: US 8,616,060 B2
(45) Date of Patent: Dec. 31, 2013

(54) ACOUSTIC DEVICE FOR LOCALIZED CONTACTLESS MEASUREMENT OF ELASTIC AND DISSIPATIVE NON-LINEARITIES AND VISCOELASTICITY

(75) Inventors: Samuel Calle, Larcay (FR); Marielle Defontaine, Tours (FR); Jean-Pierre Remenieras, Montlouis (FR); Guillaume Renaud, Tours (FR)

(73) Assignee: Universite Francois Rabelais de Tours, Tours (FR)

( * ) Notice: Subject to any disclaimer, the term of this patent is extended or adjusted under 35 U.S.C. 154(b) by 261 days.

(21) Appl. No.: 13/000,128

(22) PCT Filed: Jun. 23, 2009

(86) PCT No.: PCT/FR2009/000758
§ 371 (c)(1),
(2), (4) Date: Mar. 16, 2011

(87) PCT Pub. No.: WO2010/007234
PCT Pub. Date: Jan. 21, 2010

(65) Prior Publication Data
US 2011/0154901 A1  Jun. 30, 2011

(30) Foreign Application Priority Data
Jun. 24, 2008  (FR) ..................................... 08 03542

(51) Int. Cl.
G01N 29/04 (2006.01)
G01N 29/12 (2006.01)
(52) U.S. Cl.
USPC .............................................. 73/579; 73/625
(58) Field of Classification Search
USPC .................... 73/579, 602, 658, 659, 624–629
See application file for complete search history.

(56) References Cited

U.S. PATENT DOCUMENTS

| | | | |
|---|---|---|---|
| 3,867,836 A | 2/1975 | Sessler et al. | |
| 4,819,649 A | 4/1989 | Rogers et al. | |
| 4,844,082 A | 7/1989 | Fukukita et al. | |
| 6,086,535 A * | 7/2000 | Ishibashi et al. | 600/439 |

(Continued)

OTHER PUBLICATIONS

Renaud G. et al.; "Non-linear Acoustic Measurements to Assess Crack Density in Trabecular Bone;" International Journal of Non-Linear Mechanics, vol. 43, No. 3, XP022511057, Jan. 15, 2008; pp. 194-200.

(Continued)

*Primary Examiner* — Helen Kwok
(74) *Attorney, Agent, or Firm* — Harness, Dickey & Pierce, P.L.C.

(57) ABSTRACT

The disclosure relates to an acoustic method and device for localized, contactless, measurement of elastic and dissipative non-linearities and dynamic non-linear viscoelasticity in a medium subjected to a low-frequency acoustic stress and probed by ultrasonic pulses or wave trains. A device for measuring elastic and dissipative nonlinearities and viscoelasticity of a specimen includes an emitter for transmitting a low-frequency acoustic wave and a receiver to receive said low-frequency acoustic wave, which is capable of creating a low-frequency periodic variation of a hydrostatic pressure in the specimen; a generator to generate high-frequency ultrasonic pulses and a receiver to receive said pulses; and an analysis unit that includes a model for calculating modulations in time of flight and in amplitude of the ultrasonic pulses that are induced by the low-frequency acoustic wave passing through the specimen to quantify the elastic and dissipative non-linearities and the non-linear viscoelasticity of the specimen.

16 Claims, 3 Drawing Sheets

(56) References Cited

U.S. PATENT DOCUMENTS

| | | |
|---|---|---|
| 6,877,387 B1 | 4/2005 | Certon et al. |
| 6,880,379 B2 * | 4/2005 | Hedberg et al. ............ 73/12.01 |
| 2005/0075565 A1 * | 4/2005 | Satoh ........................ 600/437 |
| 2005/0109110 A1 | 5/2005 | Staszewski |
| 2007/0016038 A1 * | 1/2007 | Lynch et al. ................ 600/438 |
| 2007/0213614 A1 * | 9/2007 | Suzuki et al. ............... 600/443 |
| 2008/0125653 A1 * | 5/2008 | Antich et al. ............... 600/438 |
| 2009/0114019 A1 * | 5/2009 | Fatemi et al. ................. 73/587 |
| 2009/0247869 A1 * | 10/2009 | Rambod et al. ............. 600/437 |
| 2009/0249887 A1 * | 10/2009 | Gysling ..................... 73/861.18 |

OTHER PUBLICATIONS

Callé, S. et al.; "Application of Nonlinear Phenomena Induced by Focused Ultrasound to Bone Imaging;" Ultrasound in Medicine and Biology, vol. 29, No. 3, XP004420641, Mar. 1, 2003, pp. 465-472.

Zaitsev, V et al.; "Novel Nonlinear-Modulation Acoustic Technique for Crack Detection;" NDT&E International, Butterworth-Heinemann, Oxford, GB, vol. 39, No. 3, XP025109721, Apr. 1, 2006; pp. 184-194.

* cited by examiner

ACOUSTIC DEVICE FOR LOCALIZED CONTACTLESS MEASUREMENT OF ELASTIC AND DISSIPATIVE NON-LINEARITIES AND VISCOELASTICITY

CROSS-REFERENCE TO RELATED APPLICATIONS

This application is a National Phase Entry of International Application No. PCT/FR2009/000758, filed on Jun. 23, 2009, which claims priority to French Patent Application Ser. No. 0803542, filed on. Jun. 24, 2008, both of which are incorporated by reference herein.

TECHNICAL FIELD

The invention relates to a process and a contactless and localised acoustic measuring device for elastic and dissipative non-linearities and non-linear viscoelasticity in a medium subjected to low-frequency acoustic stress and probed by pulses or ultrasound wave trains. The present invention relates to the technical field of detection and quantification of the micro-damage (micro-fissures) in industrial or biological materials, especially osseous tissue. The invention also relates to the technical field of characterisation of other complex media such as consolidated or non-consolidated granular media (rocks, sand, concrete, etc.), complex fluid media (cosmetic, agri-food) or biphasic (polymers, petroleums).

BACKGROUND

Several documents are known from the prior art, describing systems for measuring acoustic non-linearity. These publications describe methods for measuring non-linear acoustic effects by subjecting the tested material to mechanical stresses of variable amplitude. In fact, application of variable mechanical stress to the tested material modifies its elastic, and sometimes dissipative, properties.

Part of these methods measures variations in propagation and amplitude speed of acoustic waves in a sample, caused by a quasi-static variation in the state of mechanical stress (hydrostatic pressure or uniaxial stress) of this sample. The other part of these methods uses the interaction of two acoustic waves and in general measures the growth of harmonics of the low-frequency wave:

N. Ichida, T. Sato, M. Linzer; *Imaging the nonlinear parameter of the medium, Ultrason.* Imaging, Vol. 5, 1983; pp. 295-299.

Z. Zhu, M. S. Roos, W. N. Cobb, K. Jensen; *Determination of the acoustic nonlinearity parameter B/A from phase measurements*; J. Acoust. Soc. Am., Vol. 74(5), 1983; pp. 1518-1521;

C. Barriere, D. Royer; *Diffraction effects in the parametric interaction of acoustic waves: application to measurements of the nonlinearity parameter B/A in liquids*; IEEE Trans. UFFC, Vol. 48 (6), 2001, pp. 1706-1715;

C M. Sehgal, R. C Bahn, J. F. Greenleaf; *Measurement of the acoustic nonlinearity parameter B/A in human tissues by a thermodynamic method*; J. Acoust. Am. Soc, Vol. 76(4), 1984; pp. 1023-1029;

V. Zaitsev, V. Nazarov, V. Gusev and B. Castagnede; *Novel nonlinear modulation acoustic technique for crack detection*; NDT&E International, 39 (2006) 184-194;

G. Gremaud, M. Bujard, and W. Benoit; *The coupling technique: A two-acoustic wave method for the study of dislocation dynamics*; J. Appl. Phys. 1987 61(5), 1795-1805.

However, such measuring systems have a number of disadvantages:

Techniques utilising a quasi-static test machine (needing contacting of the sample with the device) are not applicable to fluid media, gels and to living media (biomedical applications in vivo). Those dry-medium methods needing contact (adhesion for example) of the ultrasound transducers with the samples, and thus altering their surfaces, are not compatible with some applications, especially biomedical applications. Those methods employing an ultrasound wave emitted continuously can generate stationary waves complexing measurement analysis.

In the case of collinear interaction between the low-frequency wave and the ultrasound wave, there can be zones of acoustic shade in the low-frequency field created by ultrasound transducers. Those methods employing collinear interaction between the low-frequency wave and the ultrasound wave, and where the ultrasound wave must complete one or more return trips in the sample, are applicable to sharply attenuating media such as osseous tissue. Those methods employing a mechanical device in contact for varying stresses in the sample, without using mechanical resonance of this sample, have a limited range of use in terms of deformation speed (at most a few kHz).

Those methods employing a mechanical device in contact for varying stresses in the sample, using mechanical resonance of this sample, can reach deformation frequencies of a few tens of kHz, however the mechanical resonance frequency is conditioned by the geometric dimensions and the physical properties of the sample. Those methods varying the hydrostatic pressure by bearings and needing to enclose the tested sample in a hermetically sealed enclosure filled with liquid have a relatively complex conception and usage.

Those methods, not utilising a low-frequency acoustic wave to generate variations in stress, experience difficulty in conducting a test in compression and traction at the same time (or compression and relief). In the case of test machines, the holding device alters the sample. In the case of hermetically sealed enclosures, a drop in hydrostatic pressure less than atmospheric pressure requires relatively complex conception.

SUMMARY

The aim of the present invention is to rectify the disadvantages of the prior art by proposing a method and a localised and contactless measuring device of elastic and dissipative non-linearities and of the viscoelasticity of a sample subjected to external stresses. According to another aspect, the present invention also allows considering the measuring of elastic and dissipative non-linearities and viscoelasticity in fields of application where contact with the measuring system is unwanted, such as agri-food and biomedical applications. Alternatively, the present invention also allows considering the quantification of the damage to a material, especially for industrial or medical applications.

The invention also aims to measure these instantaneous variations in elasticity and attenuation as a function of the instantaneous variation of external stress during the phases of compression and traction of the sample, as well as quantifying the viscoelastic performance of the sample analysed. For this to happen, external stresses applied to the sample are generated by a low-frequency acoustic wave whereof the wavelength is clearly greater than the size of the sample in the medium holding the sample. The variations in hydrostatic pressure generated this way compress and relax the sample in three spatial directions. Simultaneously, a series of ultrasound pulses (high-frequency) is transmitted through the sample to measure the variations in propagation and attenuation speed of the medium associated with variations in hydrostatic pressure.

More precisely, the object of the invention is an acoustic measuring device, localised and contactless, of elastic and dissipative non-linearities and viscoelasticity of a sample. This device comprises a tank capable of receiving the sample, emission means of a low-frequency acoustic wave for creating a periodic low-frequency variation in hydrostatic pressure in the sample, measuring means capable of measuring the low-frequency acoustic wave generated by the emission means, high-frequency ultrasound pulse generating means, reception means arranged such that the high-frequency ultrasound pulses having passed through the sample are received by the reception means, and an analysis unit comprising a calculation module of modulations of time of flight and of the amplitude of the ultrasound pulses caused by passage of the low-frequency acoustic wave in the sample, so as to quantify the elastic and dissipative non-linearities as well as the viscoelasticity of the sample.

Advantageously, the device comprises a multi-parametric module imaging of viscoelastic effects (tan($\phi$)) and non-linear acoustic elastic ($\alpha$, $\beta$ and $\delta$) and dissipative effects. The generating means of the low-frequency acoustic wave preferably comprise a vibrating pot for the resonating of a dedicated piston. Alternatively, the generating means of the low-frequency acoustic wave comprise an acoustic projector. Advantageously, the emission means of high-frequency ultrasound pulses and the generating means of the low-frequency acoustic wave are oriented such that the propagation directions of ultrasound pulses and the low-frequency acoustic wave are perpendicular.

The device preferably comprises instantaneous representation means of viscoelastic and dissipative non-linearities as a function of the phases of compression and relief of the low-frequency hydrostatic pressure. The invention also relates to an acoustic measuring method, localised and contactless, of elastic and dissipative non-linearities and of the viscoelasticity of a sample arranged in a tank, comprising an emission step of a low-frequency acoustic wave for creating a periodic low-frequency variation of hydrostatic pressure in the sample, a step for measuring the low-frequency acoustic wave generated by the emission means, a step for generating high-frequency ultrasound pulses passing through the sample, a step for receiving high-frequency ultrasound pulses having passed through the sample, and a quantification step, via an analysis unit comprising a calculation module of modulations of time of flight and of the amplitude of the ultrasound pulses caused by the passage of the low-frequency acoustic wave in the sample, elastic and dissipative non-linearities as well as of the viscoelasticity of the sample. Advantageously, the analysis unit executes instantaneous calculation of the non-linear elastic and dissipative effects as well as representation of the complex viscoelastic performance of the sample during the traction and compression phases of the low-frequency hydrostatic pressure.

According to particular embodiments, instantaneous calculation of non-linearities is executed as a function of either the amplitude or deformation speed during the traction and compression phases of the low-frequency hydrostatic pressure. Advantageously, the analysis unit executes the calculation of the frequential components (zero frequency: order 0; fundamental frequency: order 1; double frequency: order 2) of elastic and dissipative non-linearities as a function of the average amplitude of the low-frequency hydrostatic pressure. Advantageously, the frequency of the low-frequency acoustic wave is a few Hz and 100 kHz, the ultrasound pulses exhibit a frequency range of 20 kHz to 100 MHz and a firing rate around 10 times greater than the frequency of the low-frequency acoustic wave, with the aim of correctly sampling the traction/compression periods of the low-frequency wave.

The analysis unit preferably processes a sequence resulting from the averaging of 2 to 100 firings of trains of low-frequency acoustic wave and successive high-frequency pulses. Advantageously, the method comprises a step for instantaneous representing of viscoelastic and dissipative non-linearities as a function of the phases of compression and relief of the low-frequency hydrostatic pressure.

The fact of generating variation in the hydrostatic pressure inside the tank using a low-frequency acoustic wave interacting synchronously in the sample with a ultrasound "probe" wave results in instantaneous measurement of viscoelastic effects and non-linear elastic and dissipative effects in the sample. Using an acoustic wave to generate variations in hydrostatic pressure in the medium allows dynamic study of the non-linear acoustic effects during the successive phases of traction and compression of the sample. According to the type of sample analysed, hysteresis can be optionally measured between the phases of increase and decrease in hydrostatic pressure.

Linking a piston to a vibrating pot enables design and execution of generating means of the low-frequency wave with wide latitude for the choice of deformation speed. In fact, the geometric and structural parameters of the piston determine its resonance frequency. Using an acoustic projector (submarine loudhailer) could advantageously replace the vibrating pot/piston system, the frequency of the low-frequency acoustic wave no longer being dependent on the piston. Using a low-frequency acoustic wave to vary hydrostatic pressure conditions homogeneously in three spatial dimensions "probes" the sample by varying the propagation direction of the ultrasound wave probe and thus studying anisotropy of viscoelastic and dissipative non-linearities of the medium.

Contactless generation in the medium of low-frequency stress in traction and compression using an acoustic wave enables study of viscoelastic and dissipative non-linearities:
  in fluid media and non-prehensible gels in a conventional mechanical test machine;
  in media to be protected from possible external contamination (biological and agri-food media);
  in solid media with complex geometries; and
  for live application (by way of example study of micro-damage in the heel bone).

BRIEF DESCRIPTION OF THE DRAWINGS

Other characteristics and advantages of the invention will emerge from the following description of a detailed embodiment, in reference to the attached figures which illustrate respectively.

DETAILED DESCRIPTION OF AN EMBODIMENT

Figure 1:
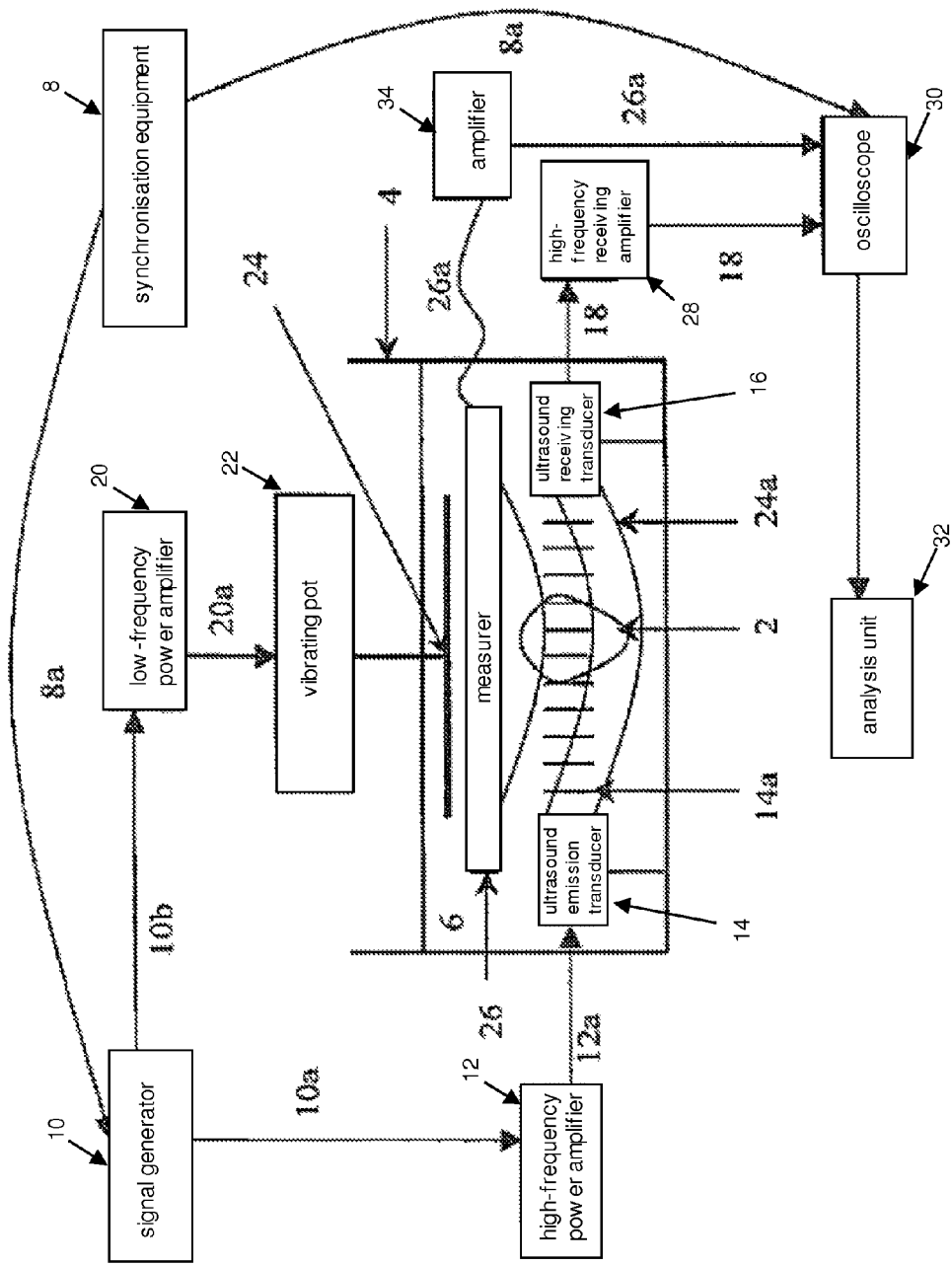
FIG. 1 is a schematic view of an embodiment of a device for measuring non-linear elastic and dissipative parameters and of the viscoelastic parameter of a sample according to the invention.

FIG. 1 illustrates an embodiment of a localised and contactless instantaneous measuring device in variations in speed and attenuation of high-frequency ultrasound pulses spreading in a sample (2) subjected to variations in hydrostatic pressure generated by a low-frequency acoustic wave. In this example, the sample (2) analysed is placed in a tank (4) filled with fluid (6) such as water. Filling the tank with water ensures correct propagation of ultrasound pulses. But water can advantageously be replaced by any other fluid.

The device comprises synchronisation equipment (8) for generating a synchronisation signal (8a), preferably in square form. This synchronisation signal (8a) allows synchronisation of a signal generator (10) and oscilloscope (30), thus ensuring perfect synchronising of measurements of high-frequency pulses and of low-frequency pressure, enabling pertinent representation of instantaneous diagrams of viscoelastic and dissipative non-linearities. The signal generator (10) comprises two paths (10a) and (10b) and delivers two synchronised signals, preferably in sinusoidal form. Alternatively, two generators can be used in place of the double-path generator (10). In this case, the two signal generators are synchronised by the synchronisation signal (8a).

The first path (10a) of this generator (10) is advantageously connected to a high-frequency power amplifier (12) and produces a high-frequency electric emission signal (12a). The high-frequency power amplifier (12) is connected to an ultrasound emission transducer (14) for transforming the high-frequency electric emission signal (12a), constituted by high-frequency electric pulses, into a train of ultrasound pulses (14a).

The frequency of the emission transducer (14) will advantageously be between 20 kHz and 100 MHz. By way of example, the nominal determined frequency for application in the heel bone is equal to 1 MHz. The emission transducer (14) is also placed in the tank (4) and arranged vis-à-vis a receiving ultrasound transducer (16) so that the ultrasound pulses (14a) passing through the sample (2) are received at the level of the receiving transducer (16). The ultrasound pulses (14a) can be constituted by a few ultrasound periods.

An electric high-frequency receiving signal (18) coming from the ultrasound receiving transducer (16) is advantageously transmitted to a high-frequency receiving amplifier (28), then digitised by the digital oscilloscope (30). The emission (14) and receiving transducers (16) can be planar or focused mono-transducers, planar or focused multi-element annular networks, or planar or focused multi-element linear networks, mono or bi-dimensional. The receiving transducer (16) can also be a hydrophone. By way of example, the results in the heel bone were obtained by means of planar monotransducers.

The second path (10b) of the generator (10) is preferably connected to a low-frequency power amplifier (20). This low-frequency power amplifier (20) transmits an amplified low-frequency electric signal (20a) to a vibrating pot (22) capable of setting in motion a piston (24) integral with the axis of the vibrating pot (22) and arranged inside the tank (4). The vibrating pot (22) generates deformation speeds of advantageously between 10 Hz and 15 kHz. By way of example, frequencies of between 2 and 5 kHz were used in relative application to the heel bone. For ideal operation, it is necessary to send a few tens of sinusoidal periods to let the piston (24) reach its maximal amplitude resonance.

The low-frequency wavelength must be clearly greater than the distance between the ultrasound sending (14) and receiving (16) transducers to be able to consider the quasi-static low-frequency pressure field throughout propagation of an ultrasound pulse (14a) between the ultrasound transducers (14) and (16). Movement of the piston (24) generates a low-frequency acoustic wave (24a), preferably sinusoidal and advantageously exhibiting a propagation direction orthogonal to the propagation direction of the ultrasound pulses (14a). This low-frequency acoustic wave (24a) generates a sinusoidal variation of the hydrostatic pressure in a localised region of the tank (4). In fact, the low-frequency wavelength (24a) is considerable vis-à-vis at least one of the dimensions of the probed sample (2).

Alternatively to an orthogonal interaction between the ultrasound pulses (14a) and the low-frequency acoustic wave (24a) it is possible to place the pair of ultrasound transducers (14) and (16) at any angle vis-à-vis the propagation direction of the low-frequency wave (24a). The configuration of an orthogonal interaction between the propagation directions of the ultrasound (14a) and low-frequency (24a) pulses enables study of the anisotropy of the non-linear parameters of the sample (4) in a plane parallel to the piston (24). Also, considering any angle between the plane of the high-frequency transducers (14, 16) and the propagation direction of the low-frequency acoustic wave (24a), we access to a study of the anisotropy of the non-linear parameters in the three spatial dimensions.

In order to maximise the variations in amplitude of the low-frequency acoustic wave (24a), the piston (24) preferably operates on its first mode of resonance. The choice of density and rigidity of the material making up the piston (24), as well as its diameter and thickness, determine its resonance frequency and produces variations in hydrostatic pressure of the order of 70 kPa. By way of example, a glass piston of diameter of 140 mm and thickness of 6 mm generates vibration at the frequency 2800 Hz and reaches variations in amplitude of hydrostatic pressure of 70 kPa at 15 mm of the surface of the piston. The emission means of the low-frequency acoustic wave (24a) could alternatively be composed of a submarine or sonar loudhailer (acoustic projector) to reach deformation speeds greater than 15 kHz while maintaining high levels of pressure.

The variations in low-frequency hydrostatic pressure are measured by means of a hydrophone (26) placed parallelly to the piston in the plane of the high-frequency transducers (14) and (16). This way, the low-frequency wave generated in the tank (4) is measured by this hydrophone (26). The low-frequency electric signal (26a) coming from the hydrophone (26) is advantageously transmitted to an amplifier (34) then communicated to the oscilloscope (30) for digitizing. The typical form of this amplified low-frequency electric signal (26a) is illustrated, by way of example, in FIG. 2. Short high-frequency wave trains (14a) pass through the sample (2) with a firing rates allowing correct sampling of the variations in hydrostatic pressure in the tank (4). Typically for a low-frequency acoustic wave (24a) of frequency 2800 Hz, a rate of ultrasound pulses (14a) of around 25 kHz is used, or around 10 ultrasound firings per period of the low-frequency acoustic wave (24a).

Figure 2:
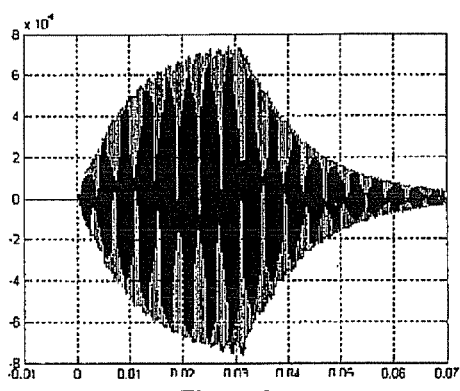
FIG. 2 shows an illustration of the hydrostatic pressure (low-frequency acoustic wave) measured by means of a hydrophone located in the tank in the same plane as the ultrasound transducers under the low-frequency piston, according to the invention.

The temporal length of the window of acquisition of the high-frequency electric receiving signals (18) and of the low-frequency electric signal (26a) is judiciously determined to record part of the signal not subjected to variations in low-frequency pressure and the total rise in resonance of the low-frequency piston. By way of example, if a piston resonating at 2800 Hz is used, a window of 70 ms is necessary to cover the whole experiment (FIG. 2). To optimise the signal to noise ratio of the high-frequency electric receiving signal (18), an averaging over N experiments is conducted by sending a train of low-frequency acoustic waves (24a) N times.

A sampling frequency of the high-frequency electric receiving signal (18) clearly greater (of the order of 10 to 50 times more) than the frequency of the ultrasound pulses (14a) is selected. By way of example a level of noise for measuring modulation of time of flight of the order of $10^{-10}$ seconds for a sampling frequency of 25 MHz, averaging N=30 and ultrasound pulses of frequency 1 MHz is obtained in water. The high-frequency electric receiving signal (18) and the low-frequency electric signal (26a) digitised by the oscilloscope (30) are then transmitted to the analysis unit (32) for storage and data processing. The analysis unit (32) processes the information contained in the high-frequency electric receiving signal (18) and the low-frequency electric signal (26a) previously digitised and synchronised so as to calculate elastic and dissipative non-linearities as well as the coefficient of viscoelasticity of the sample (2).

The elastic and dissipative non-linearities and the viscoelasticity are calculated from variations in time of flight and amplitude of the high-frequency electric receiving signal (18) as a function of the variations in low-frequency pressure. The variations in time of flight of the short ultrasound wave trains (14a), generated during the phases of compression and relief of the low-frequency hydrostatic pressure, are linked to the variations in speed of ultrasound propagation in the medium (equation 1):

$$\frac{\partial TOF}{\partial PBF} = -\frac{L}{C_0^2}\frac{\partial c}{\partial PBF} \qquad \text{Eq. 1}$$

where,
L is the distance between the sending and receiving ultrasound transducers (14) and (16);
TOF (Time Of Flight) is time of propagation of high-frequency pulses (14a) between the ultrasound transducers (14) and (16);
c is the speed of propagation of the ultrasound wave in the relevant medium subjected to variations of low-frequency pressure;
$C_0$ is the speed of propagation of the ultrasound wave in the relevant medium in the absence of variations of low-frequency pressure;

Since the speed of ultrasound propagation is linked to the elastic module K and to the density of the relevant medium $\rho_0$, the variations in speed c or of the time of flight (TOF) as a function of the variations of K (equation 2) can be written in the same way:

$$\frac{\partial TOF}{\partial PBF} = -\frac{L}{2C_0^3 \rho_0}\frac{\partial K}{\partial PBF} \qquad \text{Eq. 2}$$

where,
K is the viscoelastic module;
$\rho_0$ is the density of the medium in the absence of variations in low-frequency pressure.

Figure 3:
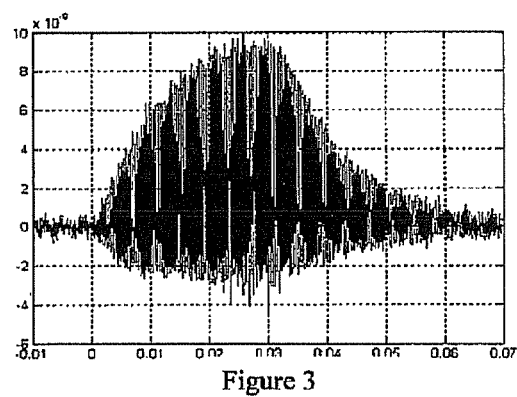
FIG. 3 shows an illustration of the calculation of the modulation of time of flight of ultrasound high-frequency wave trains, as a function of time, spreading in a human heel bone.
Figure 5:
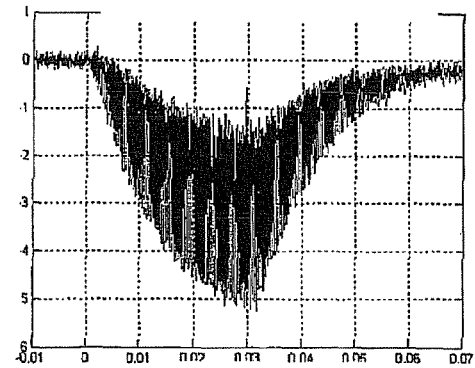
FIG. 5 shows an illustration of the rate of amplitude modulation of ultrasound high-frequency wave trains, as a function of time, spreading in a human heel bone.

The analysis unit (32) comprises a calculation module of elastic non-linearities and dissipative non-linearities of the sample (2) as a function of time, such as illustrated in FIGS. 3 and 5, respectively. The analysis unit (32) also comprises a calculation module of the viscosity parameter.

The calculation module of the non-linearities elastic applies an intercorrelation algorithm between the first high-frequency pulse coming from the high-frequency electric receiving signal (18) (corresponding to an ultrasound pulse (14a) not having been subjected to variations in low-frequency pressure) and each of the following high-frequency pulses of this electric receiving signal (18). Intercorrelation leads to the estimation of the period between the first reference high-frequency pulse and the $n^{th}$ high-frequency pulse of the electric receiving signal (18). To optimise the estimation of this period, parabolic interpolation of the intercorrelation peak is implemented with the aim of avoiding digital sampling. The final result leads to modulation of time of flight (Time Of Flight Modulation: TOFM) as a function of time (FIG. 3). Alternatively to an intercorrelation algorithm, a demodulation algorithm of the phase of signals originating from the ultrasound wave (14a) can be used in the case where the latter is sent continuously over time of firing of a train of low-frequency waves (24a).

For the calculation module of dissipative non-linearities, three approaches are possible:
1. Measuring the rate of variation in peak-to-peak amplitude of pulses of the high-frequency electric receiving signal (18) in the temporal field;
2. Measuring the rate of variation in maximal amplitude of pulses of the high-frequency electric receiving signal (18) in the frequential field (FIG. 5);
3. Measuring the rate of variation in the frequential attenuation slope.

As is the case for elastic non-linearities, the variation is calculated in each of these three cases from a pulse of the high-frequency electric receiving signal (18), the reference signal not having undergone variations of low-frequency pressure. In the case of approach 3), frequential attenuation, currently known as BUA (Broadband Ultrasonic Attenuation) in osseous applications, corresponds to the inclination of the ratio of modules of spectra of the reference signal (first pulse of the high-frequency electric receiving signal (18)) and of the $n^{th}$ pulses of the high-frequency electric receiving signal (18) on the relevant passing band. The final result leads to the rate of variation in amplitude or attenuation as a function of time (FIG. 5).

It is possible to analyse and present results according to two modalities from, on the one hand, temporal functions of the elastic and dissipative non-linearities disclosed earlier and, on the other hand, synchronised measuring of variations in low-frequency pressure as a function of time:

1) Instantaneous modality: instantaneous diagrams of elastic and dissipative non-linearities as a function of the amplitude of the low-frequency pressure or the speed of deformation of low-frequency amplitude (that is, the derivative);
2) Frequential modality: frequential analyses of elastic and dissipative non-linearities at orders 0, 1 and 2 (respectively zero frequency, fundamental resonance frequency of the piston and double frequency of the piston) as a function of the average amplitude of the low-frequency pressure.

In the case of the instantaneous modality, each measuring point of amplitude of the low-frequency pressure is synchronised with a calculation point of the modulation of the time of flight (elastic non-linearity) or of the rate of the amplitude modulation (dissipative non-linearity). These synchronised measurements naturally lead to the representation of the modulation of the time of flight or of the amplitude of the ultrasound pulses (14a) as a function of the amplitude of the low-frequency pressure, and as a result of instantaneous of viscoelastic and dissipative non-linearities during the phases of compression and relief in the sample (2). The window of analysis can be selected during the phase of a rise in resonance of the piston, on the plate once the resonance is set and/or during the relaxation phase of the piston (after the electric signal stops (10b).

Representation can be made by way of a multi-parametric tomographic imaging module in transmission positioned in a plane parallel (XoY) to the plane of the piston and displaying the viscoelastic effects (tan($\phi$)) and the elastic acoustic non-linear ($\alpha$, $\beta$, $\delta$) and dissipative effects. The device advantageously comprises a mechanical module of rotation and of translation of the sample (2) or of the pair of ultrasound transducers (14,16). However, the pair of ultrasound transducers and the associated translation system could advantageously be replaced by a network of transducers in one dimension.

Representation can also be made by a multi-parametric transverse imaging module comprising a mechanical scanning module of the sample (2) or ultrasound transducers (14,16) positioned in the plane perpendicular (YoZ) to the plane of the piston. Using a two-dimensional network of transducers linked to an electronic scanning module could advantageously replace the pair of ultrasound transducers and the mechanical scanning system.

Figure 4:
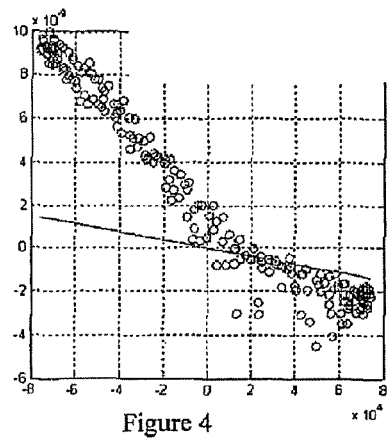
FIG. 4 shows an illustration of the instantaneous diagram of the modulation of time of flight of ultrasound pulses representing elastic non-linearities as a function of variations in low-frequency stress (hydrostatic pressure) in a heel bone.
Figure 6:
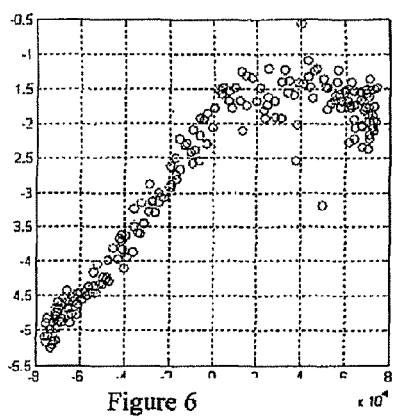
FIG. 6 shows an illustration of the instantaneous diagram of the rate of amplitude modulation of ultrasound pulses representing dissipative non-linearities as a function of the variations in low-frequency stress (hydrostatic pressure) in a human heel bone.

If the relevant sample exhibits non-linearity of hysteretic type (damaged or granular media), and if however this diagram does exhibit hysteresis, it can lead to the measuring of a viscoelasticity coefficient. The latter is obtained by means of a calculation unit of the parameter of viscoelasticity, from measuring the dephasing $\phi$ between the low-frequency pressure and the modulation of time of flight of high-frequency electric receiving signals (18). The viscoelasticity coefficient (or loss factor) currently used is tan($\phi$). By way of indication, FIGS. 4 and 6 respectively illustrate an example of modulation of the time of flight and an example of the rate of modulation in amplitude of high-frequency electric receiving signals (18) as a function of the amplitude of the low-frequency pressure within the scope of measuring a heel bone.

As is the case for a mechanical assay on a quasi-static test machine, such analysis displays distinctly and throughout the same assay viscoelastic and dissipative performances of the medium in traction for a variation in negative hydrostatic pressure, and in compression for a variation in positive hydrostatic pressure. In the case of the frequential modality, modulation of time of flight and amplitude of high-frequency electric receiving signals (18) as well as the amplitude of the low-frequency pressure as a function of time are cut out into sliding windows of sizes equal to 4 or 5 low-frequency periods during the phases of rise in resonance and descent of the piston. The windows of the two non-linear modulations (elastic and dissipative) are analysed in the frequential field, where the amplitudes of the module of these spectra are recorded for zero frequency (order 0), the fundamental resonance frequency of the piston (order 1) and the double frequency of the piston (order 2).

Figure 7A:
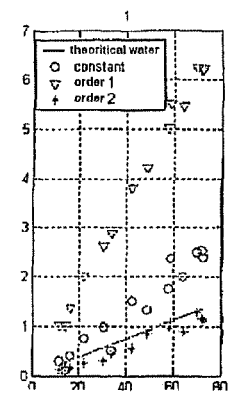
FIGS. 7a and 7b show illustrations of the modulation of time of flight and of the rate of amplitude modulation of ultrasound high-frequency wave trains, measured in the frequential field, at orders 0, 1 and 2, corresponding respectively to zero frequency, to the fundamental resonance frequency of the piston, and to the double frequency of the piston, following propagation in a human heel bone and for different levels of average low-frequency amplitude.
Figure 7B:
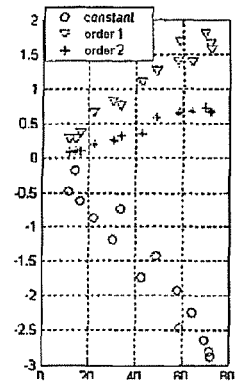

In parallel to this, the modules of the spectra of the windows corresponding to the amplitude of the low-frequency pressure lead to the calculation of the average amplitude of this low-frequency pressure. The choice of 4 to 5 low-frequency periods results from the compromise between an adequate length for calculating a pertinent Fourier transform and a minimal length for considering the average amplitude of the low-frequency pressure as constant. By way of indication, FIGS. 7a and 7b respectively illustrate an example of modulation of the time of flight and an example of the rate of modulation in amplitude of coded and amplified electric signals (18), obtained from measuring in the frequential field at orders 0, 1 and 2, as a function of the average amplitude in low-frequency pressure within the scope of measuring a heel bone.

Contrary to the instantaneous modality, the information linked to the phases of traction and compression is no longer accessible, as the amplitude of the low-frequency pressure is averaged over a few periods in the Fourier field. However, frequential analysis results in decomposition of non-linearities according to different frequential orders: constant, fundamental and harmonic. Also, it allows study of the possibly different performances during the phases of increase and decrease in low-frequency amplitude, during resonance of the piston.

A phenomenological relation (K. R. McCall and R. A. Guyer; *Equation of state and wave propagation in hysteretic nonlinear elastic materials*; Journal of Geophysical Research, Vol. 99(B12), 1984; pp. 23 887-23 897.) based on development in series of Taylor to the order 2 of the elastic module K as a function of low-frequency pressure, modified to take into account unconventional or hysteretic non-linear effects, is utilised to extract or identify conventional non-linear $\beta$, $\delta$ (orders 1 and 2) and non conventional a parameters according to the equation:

$$K = K_0 + \beta \cdot PBF - \delta \cdot \frac{PBF^2}{K_0} + \alpha(\Delta(PBF) - PBF \cdot \text{sign}(PBF)) \qquad \text{Eq. 3}$$

where:
Ko is the linear elastic module;
PBF is the temporal derivative of low-frequency pressure. This identification can be made from adjustment on the instantaneous diagram connecting the modulation of time of flight (or elastic) to variations in low-frequency pressure.

The invention is not limited to the embodiments as described and illustrated. It is also possible to provide embodiments for which the tank (4) would contain an element in gaseous phase and not liquid phase. Also, the different embodiments of the analysis unit (32) as well as the results obtained in these modes can be combined in different ways without departing from the scope of the invention.

The invention claimed is:
1. A localized and contactless acoustic measuring device to measure elastic and dissipative non-linearities and viscoelasticity of a sample, the device comprising:

a tank operably taking up the sample;

an emitter of a low-frequency acoustic wave capable of creating a periodic low-frequency variation of a hydrostatic pressure in the sample;

a measurer operably measuring the variation of the hydrostatic pressure due to the low-frequency acoustic wave generated by the emitter;

a generator of high-frequency ultrasound pulses;

a receiver arranged vis-à-vis the generator such that the high-frequency ultrasound pulses having passed through the sample are received and measured by the receiver;

a synchronization equipment to generate a synchronization signal to synchronize the measurements of the high-frequency ultrasound pulses and the variation of the hydrostatic pressure; and an analysis unit comprising a calculation module to calculate modulations of time of flight and of amplitude of the ultrasound pulses caused by passage of the low-frequency acoustic wave in the sample to quantify the elastic and dissipative non-linearities and the viscoelasticity of the sample.

2. The acoustic measuring device of claim 1, further comprising a multi-parametric imaging module to generate a representation of viscoelastic effects and of non-linear acoustic elastic effects and dissipative effects.

3. The acoustic measuring device of claim 1, wherein the emitter of the low-frequency acoustic wave comprises a vibrating pot for resonating a dedicated piston capable of creating the periodic low-frequency variation.

4. The acoustic measuring device of claim 1, wherein the emitter of the low-frequency acoustic wave comprises an acoustic projector operably creating the low-frequency variation.

5. The acoustic measuring device of claim 1, wherein the generator of the high-frequency ultrasound pulses and the emitter of the low-frequency acoustic wave are oriented such that propagation directions of the ultrasound pulses and of the low-frequency acoustic wave are perpendicular.

6. The acoustic measuring device of claim 1, wherein the analysis unit operably instantaneously represents the viscoelasticity and dissipative non-linearities as a function of phases of compression and relief of the periodic low-frequency variation of the hydrostatic pressure.

7. The acoustic measuring device of claim 1, wherein the analysis unit operably conducts representation of frequential components, zero frequency (order 0), a fundamental resonance frequency (order 1) and a double frequency of a piston (order 2), of the elastic and dissipative non-linearities as a function of an average amplitude of the periodic low-frequency variation of the hydrostatic pressure.

8. A localized and contactless acoustic measuring method to measure elastic and dissipative non-linearities and viscoelasticity of a sample arranged in a tank, the method comprising:

emitting a low-frequency acoustic wave to create a periodic low-frequency variation of a hydrostatic pressure in the sample;

measuring the variation of the hydrostatic pressure due to the low-frequency acoustic wave;

generating high-frequency ultrasound pulses passing through the sample;

receiving and measuring the high-frequency ultrasound pulses having passed through the sample;

synchronizing the measurements of the high-frequency ultrasound pulses and the variation of the hydrostatic pressure; and calculating modulations of time of flight and of amplitude of the ultrasound pulses caused by passage of the low-frequency acoustic wave in the sample to quantify the elastic and dissipative non-linearities and the viscoelasticity of the sample.

9. The acoustic measuring method of claim 8, further comprising representing instantaneous values of the viscoelasticity and dissipative non-linearities as a function of phases of compression and relief of the periodic low-frequency variation of the hydrostatic pressure.

10. The acoustic measuring method of claim 8, further comprising representing frequential components, zero frequency (order 0), a fundamental resonance frequency (order 1) and a double frequency of a piston (order 2), of the elastic and dissipative non-linearities as a function of an average amplitude of the periodic low-frequency variation of the hydrostatic pressure.

11. The acoustic measuring method of claim 8, further comprising quantifying a level of damage of the sample.

12. The acoustic measuring method of claim 8, wherein a frequency of the low-frequency acoustic wave is between 2 Hz and 100 kHz, the ultrasound pulses exhibiting a frequency range from 20 kHz to 100 MHz and a firing rate around 10 times greater than the frequency of the low-frequency acoustic wave.

13. The acoustic measuring method of claim 8, further comprising using an analysis unit to process a sequence resulting from an averaging of 2 to 100 successive firings of trains of the low-frequency acoustic wave.

14. The acoustic measuring device of claim 1, wherein a wavelength of the low-frequency acoustic wave is greater than a distance between the generator and the receiver.

15. The acoustic measuring device of claim 1, wherein a wavelength of the low-frequency acoustic wave is greater than a size of the sample in a medium holding the sample.

16. The acoustic measuring device of claim 1, wherein the sample is placed in (i) fluid media and non-prehensible gels in a mechanical test machine, (ii) media to be protected from external contamination, or (iii) solid media with complex geometries.

* * * * *